United States Patent
Priemer et al.

(10) Patent No.: US 7,435,224 B2
(45) Date of Patent: Oct. 14, 2008

(54) EXTRACTION OF HEART SOUND OF FETUS FROM HEART SOUND INFORMATION THAT COMPRISES PLURALITY OF MIXTURES OF PLURALITY OF HEART SOUNDS OF PLURALITY OF FETUSES

(75) Inventors: Roland Priemer, Des Plaines, IL (US); Vivek Nigam, Chicago, IL (US)

(73) Assignee: The Board of Trustees of the University of Illinois, Urbana, IL (US)

( * ) Notice: Subject to any disclaimer, the term of this patent is extended or adjusted under 35 U.S.C. 154(b) by 449 days.

(21) Appl. No.: 10/892,748

(22) Filed: Jul. 16, 2004

(65) Prior Publication Data

US 2005/0113708 A1 May 26, 2005

Related U.S. Application Data

(60) Provisional application No. 60/537,941, filed on Jan. 21, 2004, provisional application No. 60/488,311, filed on Jul. 18, 2003.

(51) Int. Cl.
*A61B 5/02* (2006.01)

(52) U.S. Cl. ..................... 600/528

(58) Field of Classification Search ................ 600/528, 600/586, 511, 513; 607/902
See application file for complete search history.

(56) References Cited

U.S. PATENT DOCUMENTS 4,781,200 A * 11/1988 Baker ........................ 600/483
4,898,179 A * 2/1990 Sirota ........................ 600/483
5,123,420 A * 6/1992 Paret ......................... 600/511
5,515,865 A * 5/1996 Scanlon ..................... 600/534
5,718,227 A * 2/1998 Witlin et al. ................ 600/528
5,807,271 A * 9/1998 Tayebi et al. ............... 600/511
5,885,222 A * 3/1999 Kassal et al. ............... 600/528
6,454,716 B1 * 9/2002 Zumeris ..................... 600/453
2001/0034490 A1 * 10/2001 Bryant et al. ............... 600/528
2003/0187364 A1 * 10/2003 Hamilton et al. ........... 600/511
2004/0243015 A1 * 12/2004 Smith et al. ................ 600/511

FOREIGN PATENT DOCUMENTS

GB 2 162 644 2/1986
WO WO 03/003905 1/2003

OTHER PUBLICATIONS

Krishna G. Ramachandran; Cardiac Sound Separation; Sep. 2002; 227 pgs.; Chicago, Illinois.
Varady, P. et al, "An Advanced Method in Fetal Phonocardiography" Computer Methods and Programs in Biomedicine, vol. 71, No. 3, Jul. 2003, pp. 283-296, Hungary.
Moghavveni, M. et al, "A Non-Invasive PC-based Measurement of Fetal Phonocardiography", Sensors and Actuators, Elsevier Sequoia S.A., vol. 107, No. 1, Oct. 1, 2003 pp. 96-103.

(Continued)

*Primary Examiner*—Carl H. Layno
*Assistant Examiner*—Jon-Eric C. Morales
(74) *Attorney, Agent, or Firm*—Robert J. Brill, Esq.; Wood, Phillips, Katz, Clark & Mortimer

(57) ABSTRACT

A heart sound analyzer component of an apparatus in one example extracts a heart sound of a fetus from heart sound information that comprises a plurality of mixtures of a plurality of heart sounds of a plurality of fetuses.

20 Claims, 8 Drawing Sheets

Block diagram of fetal phonocardiogram analyzer

OTHER PUBLICATIONS

Komaromy, B. et al., "Die Bedeutung und die Moglichkeiten der fruhzeitigen Erkennung einer Zwillingsschwangerschaft", Zentralblatt Fur Gynakologie, vol. 91, No. 42, Oct. 18, pp. 1378-1387, Germany.

* cited by examiner

System to separate phonocardiograms of multiple fetuses

Block diagram of fetal phonocardiogram analyzer

Illustration depicting two fetuses, sensor locations, and fetal phonocardiogram propagation delays Neural network structure Block diagram of fetal phonocardiogram separator Phonocardiograms of two fetuses Two mixtures of delayed fetal phonocardiograms Fetal phonocardiograms obtained from mixtures of delayed fetal phonocardiograms after processing 20 frames of data

EXTRACTION OF HEART SOUND OF FETUS FROM HEART SOUND INFORMATION THAT COMPRISES PLURALITY OF MIXTURES OF PLURALITY OF HEART SOUNDS OF PLURALITY OF FETUSES

CROSS-REFERENCE TO RELATED APPLICATIONS

This application claims the priority of U.S. provisional Patent Application Ser. No. 60/488,311 (by Roland Priemer, filed Jul. 18, 2003, and entitled "CARDIAC SOUND SEPARATOR AND STETHOSCOPE").

This application claims the priority of U.S. provisional Patent Application Ser. No. 60/537,941 (by Roland Priemer, filed Jan. 21, 2004, and entitled "EXTRACTION OF ONE OR MORE DISCRETE HEART SOUNDS FROM HEART SOUND INFORMATION").

This application contains subject matter that is related to the subject matter of the following applications, which are assigned to the same assignee as this application. The below-listed applications are hereby incorporated herein by reference in their entireties.

U.S. application Ser. No. 10/893,627 (by Roland Priemer, filed Jul. 16, 2004, entitled "EXTRACTION OF ONE OR MORE DISCRETE HEART SOUNDS FROM HEART SOUND INFORMATION").

International Application No. PCT/US 04/23049 (by Roland Priemer, filed Jul. 16, 2004, entitled "IDENTIFICATION OF ONE OR MORE DISTINCT HEART SOUND SOURCES THAT PRODUCE ONE OR MORE DISCRETE HEART SOUNDS").

International Application No. PCT/US 04/22738 (by Priemer, et al., filed Jul. 16, 2004, entitled "HEART SOUND ANALYZER COMPONENT THAT EXTRACTS HEART SOUND OF FETUS FROM HEART SOUND INFORMATION THAT COMPRISES PLURALITY OF MIXTURES OF PLURALITY OF HEART SOUNDS OF PLURALITY OF FETUSES").

TECHNICAL FIELD

This invention relates generally to the medical arts and more particularly to sensing of heart sound information.

BACKGROUND

A multiple gestation is a pregnancy in which a woman carries more than one fetus. Multiple gestations are concerning because women who are expecting more than one baby are at increased risk of certain pregnancy complications, including preterm delivery. Some of the complications associated with multiple gestation can be minimized if they are detected and diagnosed early.

The embryonic heart starts beating twenty-two days after conception. The heart at this stage may be too small to hear. By the ninth or tenth week after the last menstrual period of the expecting mother, one is more likely to be able to hear the heartbeat of the fetus. By the twelve week, the heartbeat can usually be heard consistently by using a Doppler instrument for amplification.

Although the human ear is unequalled in detecting sounds over a particular frequency range, the spectrum occupied by fetal heart sounds is on the threshold of audibility. This aural processing has always caused problems relating to degree and accuracy of fetal auscultation. Electronically processing the fetal phonocardiogram ("FPCG") presents a way of avoiding these problems. The greater low frequency sensitivity of the phonocardiographic transducer captures all the acoustic information generated by the fetal heart. Then, additional visual examination of the FPCG provides an effective way of determining temporal measures of fetal cardiac function.

The FPCG allows the measurement of the instantaneous fetal heart rate, beat-to-beat differences and duration of systolic and diastolic phases. These measures are sensitive indicators of cardiac function, reflecting fetal well-being. With the record of various critical cardiac activities readily available, some abnormalities of the fetal heart can be detected in the early stages of the pregnancy. A problem arises with the detection of the abnormalities of the fetal heart in the event of a multiple gestation. When more than one fetus is present in a mother's womb, the acoustic transducer (acoustic or electronic stethoscope) captures multiple FPCGs. As one shortcoming, it is difficult to clearly discern the heart sounds from one fetus in the mother's womb from the heart sounds of another fetus in the mother's womb.

Thus, a need exists for a capability to discern a heart sound of one fetus from the heart sound of another fetus.

SUMMARY

The invention in one implementation encompasses an apparatus. The apparatus comprises a heart sound analyzer component that extracts a heart sound of a fetus from heart sound information that comprises a plurality of mixtures of a plurality of heart sounds of a plurality of fetuses.

Another implementation of the invention encompasses an apparatus. The apparatus comprises a plurality of sensor pods of a stethoscope sensor head that are employable to capture a plurality of mixtures of a plurality of heart sounds of a plurality of fetuses that allow extraction of a heart sound of a fetus from the plurality of mixtures of the plurality of heart sounds of the plurality of fetuses.

Yet another implementation of the invention encompasses a method. Heart sound information is obtained that comprises a plurality of mixtures of a plurality of heart sounds of a plurality of fetuses. A heart sound of a fetus extracted from the heart sound information.

DESCRIPTION OF THE DRAWINGS

Features of exemplary implementations of the invention will become apparent from the description, the claims, and the accompanying drawings in which:

DETAILED DESCRIPTION

Figure 1:
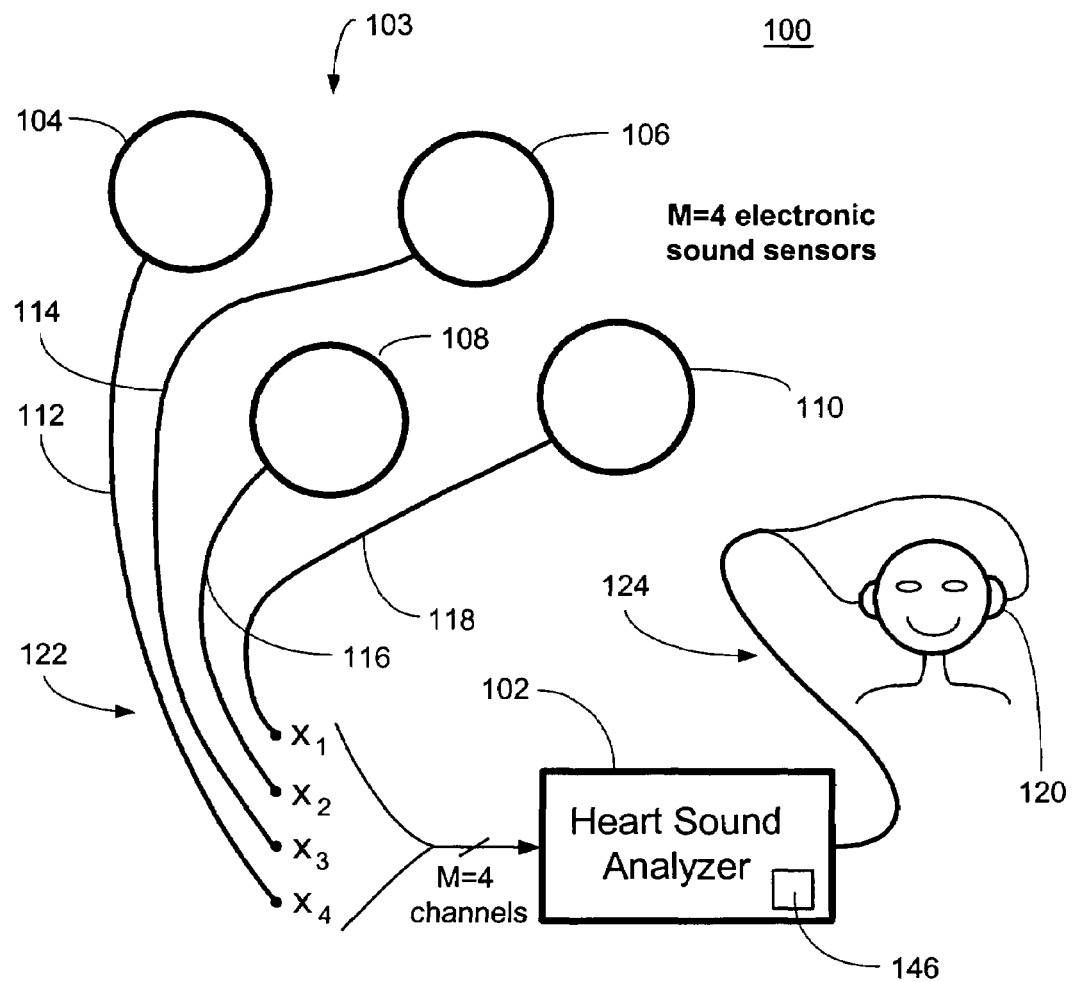
FIG. 1 is a representation of one exemplary implementation of an apparatus that comprises a heart sound analyzer, a sensor array of a plurality of sensors, a plurality of signal paths, and one or more speaker components.

Turning to FIG. 1, an apparatus 100 in one example comprises a heart sound analyzer 102, a sensor array 103 of a plurality of sensors 104, 106, 108, and 110, a plurality of signal paths 112, 114, 116, and 118, and one or more speaker components 120. The sensors 104, 106, 108, and 110 in one example obtain heart sound information 122 from a plurality of fetal hearts. The heart sound information 122 comprises a plurality of mixtures of a plurality of heart sounds of a plurality of fetuses. For example, the sensors 104, 106, 108, and 110 each capture fetal phonocardiograms ("FPCGs") from the hearts of the plurality of fetuses within a womb of a woman. The heart sound information 122 comprises mixtures of heart sounds from the plurality of fetuses. The sensors 104, 106, 108, and 110 pass the heart sound information 122 through the signal paths 112, 114, 116, and 118 to the heart sound analyzer 102. The heart sound analyzer 102 extracts a heart sound 124 of a fetus from the heart sound information 122 for aural examination by a doctor. For example, the heart sound 124 represents a heartbeat of a single fetal heart substantially without interference from heartbeats of the other fetal hearts within the womb. The heart sound analyzer 102 separates the heart sound 124 from one or more other sounds of the heart sound information 122. The heart sound analyzer 102 in one example comprises a fetal phonocardiogram analyzer.

The plurality of fetuses may comprise twins, triplets, quadruplets, quintuplets, or more. For example, the heart sound information 122 may comprise a mixture of two, three, four, five, or more fetal hearts. To extract the heart sound 124 associated with a single fetal heart, the apparatus 100 comprises a number of the plurality of sensors 104, 106, 108, and 110 at least equal to a number of the plurality of fetuses. In one example, the apparatus 100 comprises a number of the plurality of sensors 104, 106, 108, and 110 greater than a number of the plurality of fetuses. For example, the plurality of fetuses may comprise two fetuses and the apparatus 100 may comprise three sensors to allow separation of background noise, or the like, from the output of the heart sound 124 of one of the plurality of fetuses. The sensors in one example comprise microphones. The microphones capture the heart sound information 122.

Figure 2:
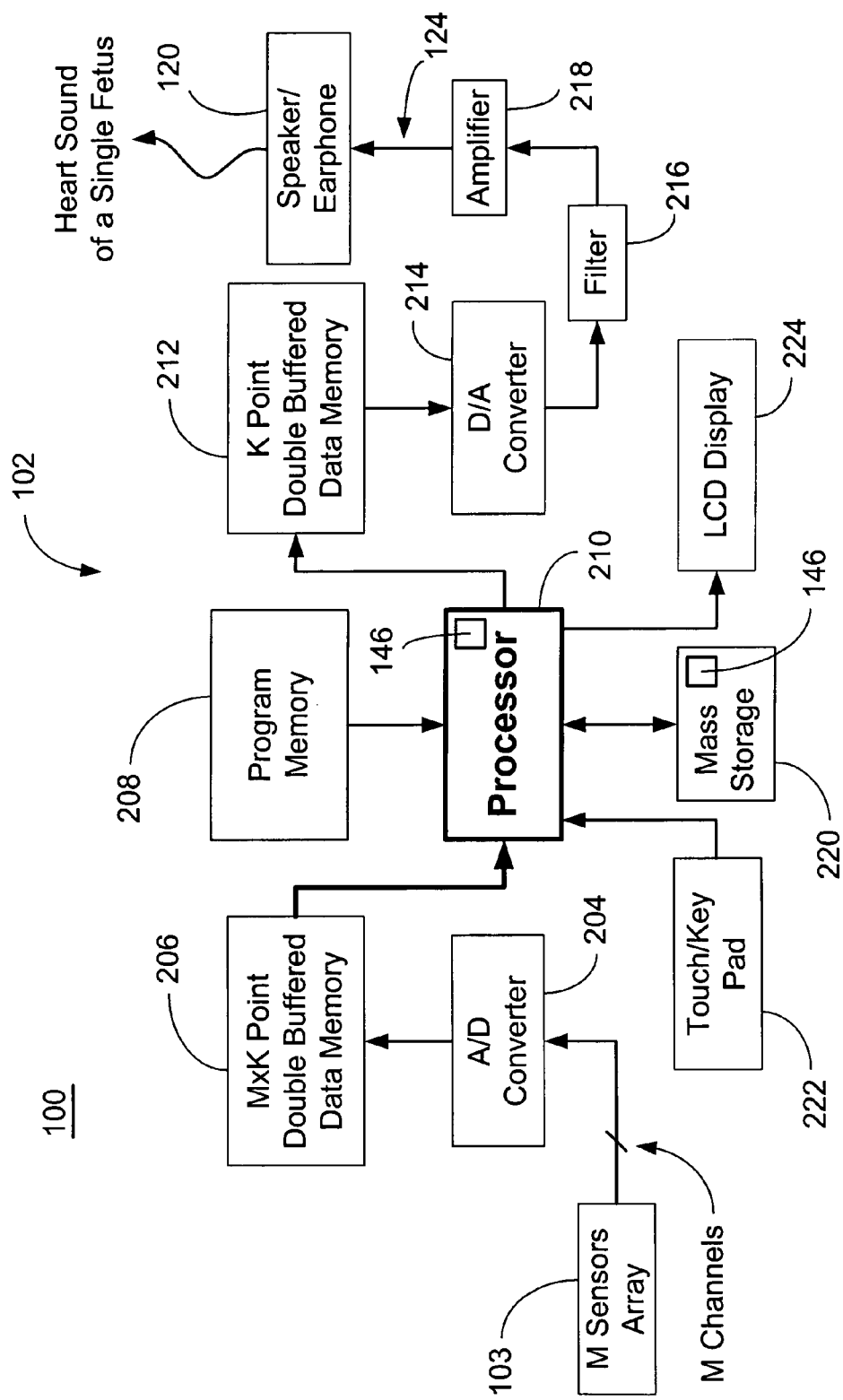
FIG. 2 is a representation of the heart sound analyzer of the apparatus of FIG. 1, and illustrates one or more analog to digital converters, one or more data buffer components, one or more software memory components, one or more processor components, one or more digital to analog converters, one or more filters, one or more amplifiers, one or more storage devices, one or more input devices, and one or more output devices.

Referring to FIGS. 1-2, the heart sound analyzer 102 comprises one or more analog to digital converters 204, one or more data buffer components 206 and 212, one or more software memory components 208, one or more processor components 210, one or more digital to analog converters 214, one or more filters 216, one or more amplifiers 218, one or more storage devices 220, one or more input devices 222, and one or more output devices 224. Upon receipt of the heart sound information 122 from the sensor array 103, the heart sound analyzer 102 processes the heart sound information 122 and in one example outputs the heart sound 124.

The processor component 210 of the heart sound analyzer 102 extracts heartbeats of one or more of the plurality of fetuses from the heart sound information 122. For example, the heart sound 124 comprises a heartbeat of a first fetus of the plurality of fetuses within the womb. In one example, the heart sound information 122 comprises a plurality of mixtures of a first heartbeat of a first fetus and a second heartbeat of a second fetus. The heart sound analyzer 102 employs a blind source separation algorithm that accounts for propagation delays of the heart sound information 122 to create statistically independent outputs of one or more of the first heartbeat and the second heartbeat. The heart sound analyzer 102 in one example employs an independent component analysis procedure to extract the heart sound 124 from the heart sound information 122.

The analog to digital converter 204 in one example obtains the heart sound information 122 from the sensor array 103. The analog to digital converter 204 in one example digitizes the heart sound information 122. For example, the processor component 210 employs the analog to digital converter 204 to digitize the heart sound information 122. The analog to digital converter 204 in one example outputs an M×K matrix of data of the heart sound information 122 to the data buffer component 206, where, for example, M is the number of sensors (e.g., the sensors 104, 106, 108, and 110) in the sensor array 103 and K is the number of times the analog to digital converter 204 samples the heart sound information 122. The data buffer component 206 in one example comprises M×K point double buffered data memory.

The data buffer component 206 in one example provides the M×K matrix of data to the processor component 210. The data buffer component 206 in one example comprises a demultiplexer, first and second data buffers, and a multiplexer. The processor component 210 in one example controls the demultiplexer to steer the output of the analog to digital converter 204 to the first data buffer with an M×K matrix of data. While the first data buffer is filling with data, the processor component 210 in one example controls the multiplexer to steer data from the second data buffer to the processor component 210 until the processor component 210 has received an M×K matrix of data. The processor component 210 processes the M×K matrix of data with software stored in the software memory component 208.

After the processor 210 has completed processing the M×K matrix of data and the first data buffer has filled with data, the processor component 210 in one example controls the demultiplexer to steer data to the second data buffer with an M×K matrix of data. While the second data buffer is filling with data, the processor component 210 in one example controls the multiplexer to steer data from the first data buffer to the processor component 210 until the processor component 210 has received an M×K matrix of data. The processor component 210 again employs the software stored in the software memory component 208 to process the M×K matrix of data. By continuously reversing the roles of the first and second data buffers, the heart sound analyzer 102 can work in real time.

The software memory component 208 in one example stores software for use by the processor component 210. The processor component 210 employs the software to extract the heart sound 124 from the heart sound information 122. The software memory component 208 in one example comprises an instance of the recordable data storage medium 146. The software memory component 208 in one example stores a blind source separation algorithm that accounts for propagation delays within the heart sound information 122. The processor component 210 employs the blind source separation algorithm to extract the heart sound 124 from the heart sound information 122.

After extraction of the heart sound 124 from the heart sound information 122, the processor component 210 stores the heart sound 124. For example, the processor component 210 may store the heart sound 124 in the storage device 220. The processor component 210 may then access the heart sound 124 upon request from a user of the heart sound analyzer 102. For example, the user may employ the input device 222 to cause the processor 210 to output the heart sound 124 to the output device 224 and/or the speaker component 120. The input device 222 in one example comprise one or more of a button, a dial, a mouse, a keyboard, and/or a touch-screen. The output device 224 in one example comprise a liquid crystal display ("LCD").

The user in one example chooses with the input device 222 to listen to the heart sound 124 with the speaker component 120. In another example, the user chooses with the input device 222 to output the heart sound 124 to the output device 224. The user may also choose to filter, amplify, and/or shift a spectral content of the heart sound 124 from a first frequency range to a second frequency range with the processor component 210. In one example, the processor component 210 employs digital filtering software to filter out one or more frequency ranges of the heart sound 124. In another example, the processor component 210 amplifies one or more regions of the heart sound 124. In still another example, the processor component 210 may shift the spectral content of the heart sound 124 from a first frequency range to a second frequency range. For example, the user may hear better in the second frequency range than in the first frequency range.

The data buffer component 212 obtains data from the processor component 210. In one example, the data buffer component 212 obtains the heart sound 124 from the processor component 210. In another example, the data buffer component 212 obtains the heart sound 124 which has been spectrally modified, spectrally shifted, and/or amplified. The data buffer component 212 in one example comprises K point double buffered data memory.

The digital to analog converter 214 in one example converts a digital representation of the heart sound 124 into an analog representation of the heart sound 124. The digital to analog converter 214 in one example outputs the heart sound 124 to one or more of the speaker component 120, the filter 216, and/or the amplifier 218. The filter 216 in one example filters one or more frequency ranges of the analog representation of the heart sound 124. The filter 216 in one example comprises one or more low pass filters. The amplifier 218 in one example amplifies an output of the filter 216 to drive the speaker component 120.

The user may employ one or more of the speaker component 120 and/or the output device 224 to listen to and/or view the heart sound 124 and/or a representation of the heart sound 124. The user may employ the speaker component 120 and/or the output device 224 for examination of the heart sound 124. The user may employ the heart sound analyzer 102 to automatically diagnose one or more fetal heart dysfunctions. For example, the processor component 210 compares one or more features (e.g., signatures) of the heart sound 124 to a normal range of the features (e.g., signatures) of the heart sound 124. If the heart sound 124 is outside of the normal range, then the heart sound 124 may indicate one or more dysfunctions.

The heart sound 124 in one example is a mixture of a plurality of discrete heart sounds from a plurality of corresponding distinct heart sound sources (e.g., a heart valve) of a single fetal heart. The heart sound analyzer 102 may extract from the heart sound 124 one or more discrete heart sounds of the corresponding distinct heart sound sources, as described in "EXTRACTION OF ONE OR MORE DISCRETE HEART SOUNDS FROM HEART SOUND INFORMATION," by Priemer, co-filed herewith. For example, the heart sound 124 may comprise a first discrete heart sound from a first distinct sound source of the single fetal heart. The heart sound 124 may also comprise a second discrete heart sound from a second distinct sound source of the single fetal heart. The first and second discrete heart sounds in one example occur contemporaneously in the heart sound 124. The heart sound analyzer 102 in one example creates statistically independent outputs of one or more of the first discrete heart sound and the second discrete heart sound to allow aural examination of the individual first and second discrete heart sounds by a doctor.

Figure 3:
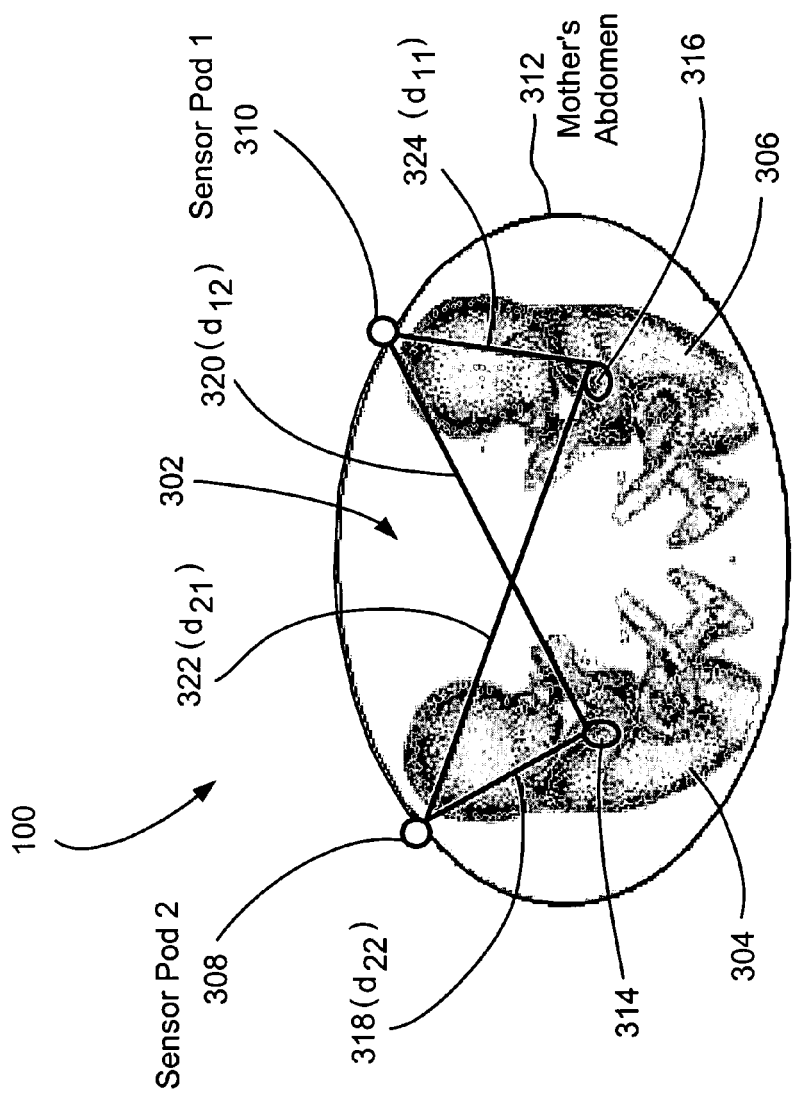
FIG. 3 is a representation of a womb of a woman that carries a plurality of fetuses that each contributes a heart sound to heart sound information captured by the plurality of sensors of the apparatus of FIG. 1.
Figure 4:
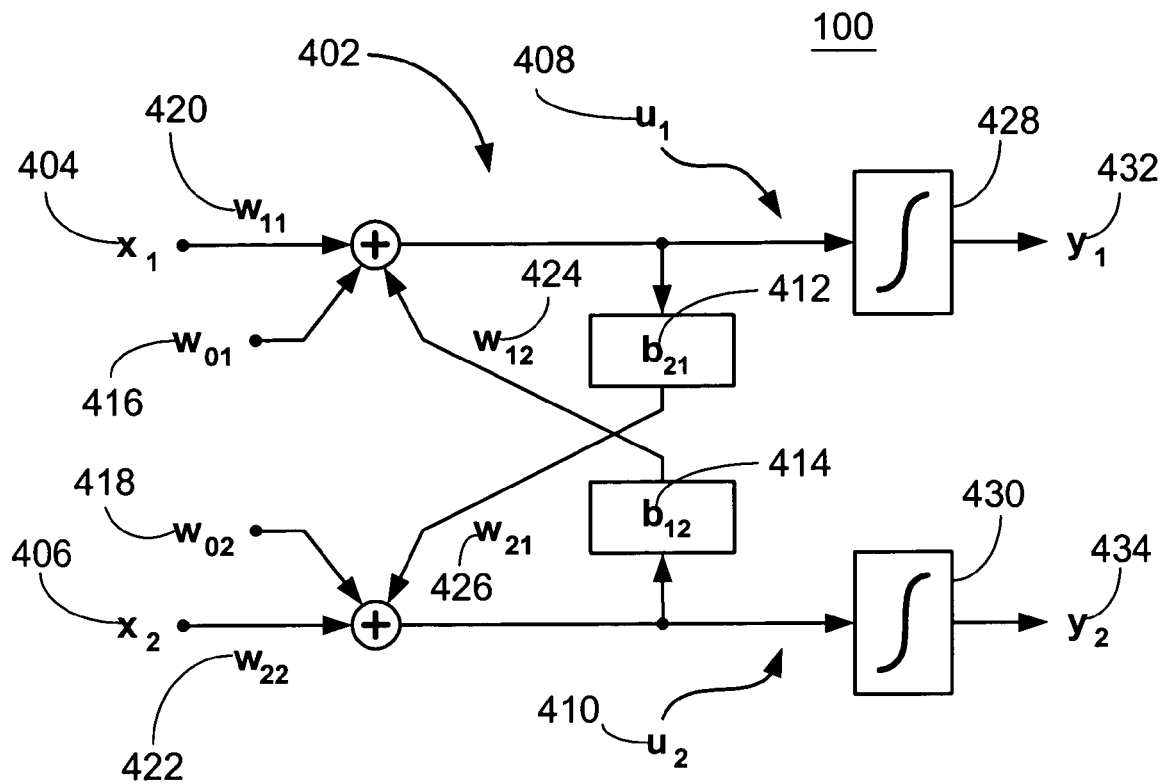
FIG. 4 is a representation of an exemplary neural network that extracts two statistically independent outputs from heart sound information captured by the plurality of sensors of the apparatus of FIG. 1.

Referring to FIGS. 1 and 3, a womb 302 of a woman may carry a plurality of fetuses 304 and 306. Each of the fetuses 304 and 306 contribute heart sounds to the heart sound information 122 captured by the sensors 104, 106, 108, and 110. The sensors 104, 106, 108, and 110 in one example are organized into a plurality of sensor pods 308 and 310. In one example, each of the sensor pods 308 and 310 comprise a single sensor or microphone. In another example, the sensor pod 308 comprises a plurality of sensors (e.g., the sensors 104 and 106) and the sensor pod 310 comprises a plurality of sensors (e.g., the sensors 108 and 110).

The sensor pods 308 and 310 are independently movable over an abdomen 312 of the woman to capture the heart sound information 122 of the fetuses 304 and 306 within the womb 302. For example, a doctor may move the sensor pod 308 over the abdomen 312 to a location that is near the fetus 304 and the doctor may move the sensor pod 310 over the abdomen 312 to a location that is near the fetus 306.

The heart sound information 122 comprises a mixture of first heart sounds from a heart 314 of the fetus 304 and second heart sounds from a heart 316 of the fetus 306. The first heart sounds from the fetus 304 experience a propagation delay ($d_{22}$) 318 traveling to the sensor pod 308 and a propagation delay ($d_{12}$) 320 traveling to the sensor pod 310. The second heart sounds from the fetus 306 experience a propagation delay ($d_{21}$) 322 traveling to the sensor pod 308 and a propagation delay ($d_{11}$) 324 traveling to the sensor pod 310. To extract the heart sound 124 from the heart sound information 122, the blind source separation algorithm accounts for the propagation delays ($d_{22}$, $d_{12}$, $d_{21}$, and $d_{11}$) 318, 320, 322, and 324 of the first and second heart sounds from the hearts 314 and 316.

Referring to FIGS. 1-4, a neural network 402 illustrates an exemplary extraction of two statistically independent outputs from the heart sound information 122 captured by two sensors (e.g., the sensors 104 and 106). The processor component 210 passes the heart sound information 122 through a plurality of external nodes of the neural network 402 in number at least equal to the number of the plurality of fetuses 304 and 306. At each external node of the plurality of external nodes, the processor component 210 passes the heart sound information 122 through a plurality of internal nodes of the neural network 402 equal to the number of external nodes to determine one or more weights and one or more delays of each of the heart sounds from the plurality of fetuses 304 and 306. For example, the neural network 406 outputs an M×K matrix of data that represents the heart sounds of the plurality of fetuses 304 and 306. The heart sounds of the plurality of fetuses 304 and 306 in one example are statistically independent.

The heart sound information 122 comprises a plurality of composite heart sounds. For example, the plurality of composite heart sounds comprise a composite heart sound signal ($x_1$) 404 captured by the sensor 104 and a composite heart sound signal ($x_2$) 406 captured by the sensor 104. The outputs of the sensors 104 and 106 are sampled at discrete time points t. The discrete time can be written as t=nT, where n is an integer and T is the time increment between samples. The sampling rate is 1/T samples/sec, and n is called the discrete time index. The composite heart sound signals ($x_1$ and $x_2$) 404 and 406 in one example comprise delayed mixtures of fetal phonocardiogram ($s_1$) produced by the fetus 306 and fetal phonocardiogram ($s_2$) produced by the fetus 304. The composite heart sound signals ($x_1$ and $x_2$) 404 and 406 in one example are modeled by:

$$x_1(t) = a_{11} s_1(t-d_{11}) + a_{12} s_2(t-d_{12})$$

$$x_2(t) = a_{21} s_1(t-d_{21}) + a_{22} s_2(t-d_{22})$$

where $d_{22}$, $d_{12}$, $d_{21}$, and $d_{11}$ represent the propagation delays 318, 320, 322, and 324 of the first and second heart sounds. Also, where $a_{11}$, $a_{12}$, $a_{21}$, and $a_{22}$ represent attenuations of the first and second heart sounds due to signal strength losses traveling through the abdomen 312 of the woman to the sensors (e.g., the sensors 104 and 106).

The neural network 402 serves to separate the composite heart sound signals ($x_1$ and $x_2$) 404 and 406 to obtain estimates ($u_1$ and $u_2$) 408 and 410 of the fetal phonocardiograms $s_1$ and $s_2$. The neural network computes:

$$u_1(t) = w_{11} x_1(t) + w_{12} u_2(t-(b_{12})) + w_{01}$$

$$u_2(t) = w_{22} x_2(t) + w_{21} u_1(t-(b_{21})) + w_{02}$$

where $b_{12}$ and $b_{21}$ represent delay differences 414 and 412 between the propagation delays 318, 320, 322, and 324. Also, where $w_{01}$, $w_{11}$, $w_{12}$, $w_{02}$, $w_{22}$ and $w_{21}$ represent weights 416, 420, 424, 418, 422, and 426 of the neural network 402.

The blocks 428 and 430 that convert the estimates ($u_1$ and $u_2$) 408 and 410 to signals ($y_1$ and $y_2$) 432 and 434 represent nonlinearities described by the equations below. A logistic function relates the estimate ($u_1$) 408 to the signal ($y_1$) 432 and the estimate ($u_2$) 410 to the signal ($y_2$) 434. For example a monotonically increasing nonlinear function converts the estimate ($u_1$) 408 to the signal ($y_1$) 432 and the estimate ($u_2$) 410 to the signal ($y_2$) 434. Below are representative logistic functions that relate the estimate ($u_1$) 408 to the signal ($y_1$) 432 and the estimate ($u_2$) 410 to the signal ($y_2$) 434:

$$y_1(t) = g(u_1(t)) = 1/(1+\exp(-u_1(t)))$$

$$y_2(t) = g(u_2(t)) = 1/(1+\exp(-u_2(t)))$$

Assuming that the fetal phonocardiograms ($s_1$ and $s_2$) are statistically independent, while composite heart sound signals ($x_1$ and $x_2$) 404 and 406 cannot be statistically independent, the parameters (e.g., the weights ($w_{01}$, $w_{11}$, $w_{12}$, $w_{02}$, $w_{22}$ and $w_{21}$) 416, 420, 424, 418, 422, and 426, and the delay differences ($b_{12}$ and $b_{21}$) 414 and 412) of the neural network 402 are calculated to make the signals ($y_1$ and $y_2$) 432 and 434 statistically independent. Then, the estimates ($u_1$ and $u_2$) 408 and 410 must also be statistically independent. If the conditions below are achieved:

$$b_{12} \to d_{12} - d_{22}, \; w_{12} w_{22} a_{22} \to -w_{11} a_{12}$$

$$b_{21} \to d_{21} - d_{11}, \; w_{11} w_{21} a_{11} \to -w_{22} a_{21}$$

then the estimate ($u_1$) 408 becomes proportional to the fetal phonocardiogram ($s_1$) and the estimate ($u_2$) 410 becomes proportional to the fetal phonocardiogram ($s_2$), delayed by the propagation delays ($d_{11}$ and $d_{22}$) 324 and 318, respectively, which means that the estimates ($u_1$ and $u_2$) 408 and 410 are statistically independent, resulting in:

$$u_1(t) \to a_{11} w_{11} s_1(t-d_{11}) \propto s_1(t-d_{11})$$

$$u_2(t) \to a_{22} w_{22} s_2(t-d_{22}) \propto s_2(t-d_{22})$$

Figure 5:
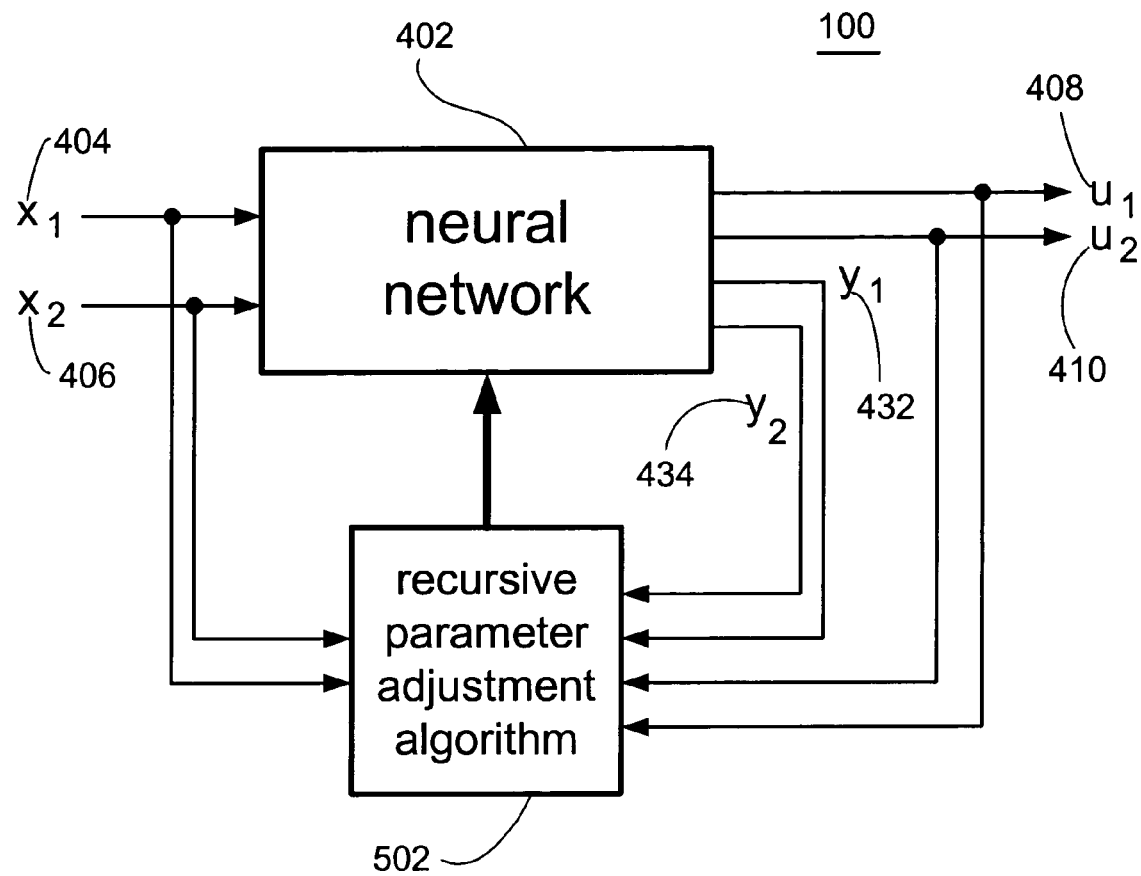
FIG. 5 is a representation of an exemplary interaction between a neural network and a recursive parameter adjustment algorithm of the heart sound analyzer of the apparatus of FIG. 1.
Figure 6:
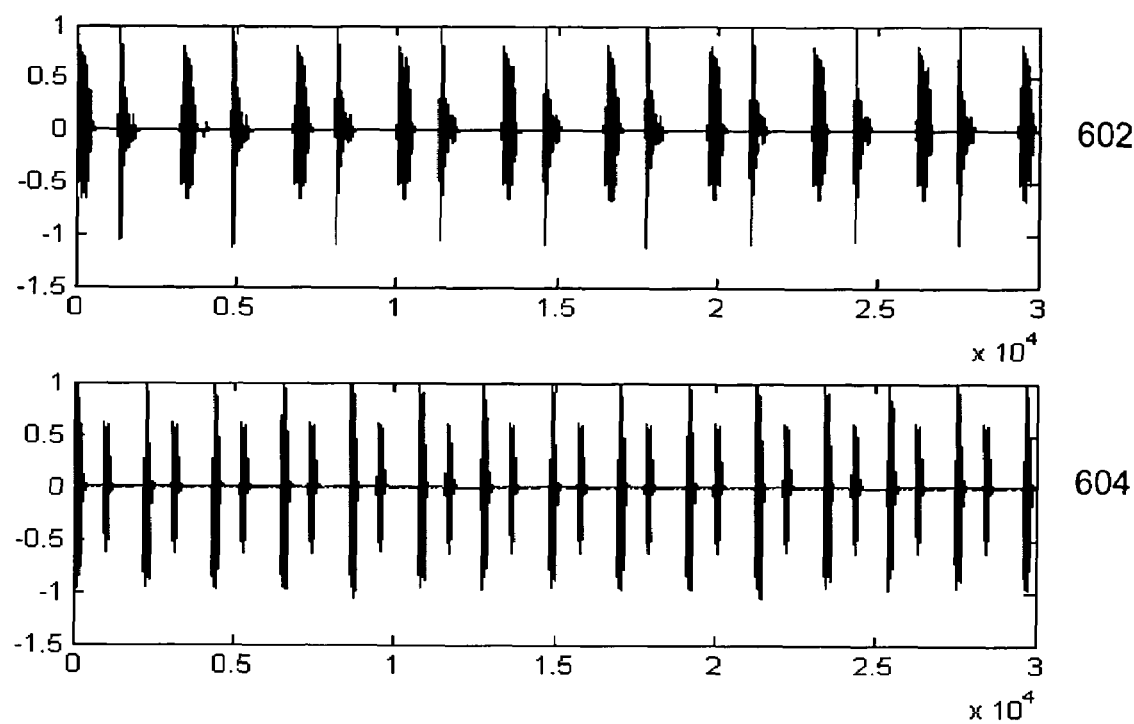
FIG. 6 is a representation of one exemplary plot of two fetal phonocardiograms that comprise heart sounds of two fetal hearts.

Determining the weights ($w_{01}$, $w_{11}$, $w_{12}$, $w_{02}$, $w_{22}$ and $w_{21}$) 416, 420, 424, 418, 422, and 426, and the delay differences ($b_{12}$ and $b_{21}$) 412 and 414 that will make the signals ($y_1$ and $y_2$) 432 and 434 statistically independent is the goal of the phonocardiogram separator depicted in FIG. 5. The recursive parameter adjustment algorithm 502 to estimate weights and delays of the neural network 402 is based on the gradients given by:

$$\Delta w_{0i} \propto (1-2y_i)$$

$$\Delta w_{ii} \propto (1-2y_i) x_i + 1/w_{ii}$$

for i=1, 2

$$\Delta w_{ij} \propto (1-2y_i) u_j(t-b_{ij})$$

$$\Delta b_{ij} \propto -(1-2y_i) w_{ij} \dot{u}_j(t-b_{ij})$$

$$\dot{u}_j(t) = u_j(t) - u_j(t-1)$$

for i, j=1,2, i≠j

The formulas above give the gradients of entropy of the signals H($y_1$, $y_2$) with respect to each of the parameters of the neural network 402. For example, consider the determination of a parameter of the neural network 402, such as the weight ($w_{11}$) 420. The gradient of H with respect to the weight ($w_{11}$) 420 is denoted by $\Delta w_{11}$.

For each input sample $x_1(t)$ and $x_2(t)$, $y_1(t)$ and $y_2(t)$ and $u_1(t)$ and $u_2(t)$ can be calculated and then $\Delta w_{11}(t)$ can also be calculated. $\Delta w_{11}$ can be calculated for many (e.g., K) input samples, and then the resulting average of $\Delta w_{11}$ can be calculated. Then, the average of $\Delta w_{11}$, denoted by $\Delta w_{11}(K)$, is used to update the value of the weight ($w_{11}$) 420 with:

$$w_{11}(\text{new}) = w_{11}(\text{old}) + h \Delta w_{11}(K)$$

where h, a small number, is called the learning rate, that is selected by trial and error. Each of the other weights ($w_{01}$, $w_{11}$, $w_{12}$, $w_{02}$, $w_{22}$ and $w_{21}$) 416, 420, 424, 418, 422, and 426, and the delay differences ($b_{12}$ and $b_{21}$) 414 and 412 are updated analogously.

Before moving on to the next set of K input samples, all the updated weights and delay differences are used to calculate $\Delta w_{11}(K)$ and the other gradients again, and then again the above equation may be used to update $w_{11}$ and all the other weights ($w_{01}$, $w_{11}$, $w_{12}$, $w_{02}$, $w_{22}$ and $w_{21}$) 416, 420, 424, 418, 422, and 426, and delay differences ($b_{12}$ and $b_{21}$) 414 and 412. This loop is continued until the absolute value of |w(new)−w(old)| for all of the weights ($w_{01}$, $w_{11}$, $w_{12}$, $w_{02}$, $w_{22}$ and $w_{21}$) 416, 420, 424, 418, 422, and 426 and |b(new)−b(old)| for all of the delay differences ($b_{12}$ and $b_{21}$) 414 and 412 becomes smaller than some predetermined threshold or the loop has been executed more than a predetermined number of times.

The blind source separation algorithm that accounts for the propagation delays of the heart sound information 122 comprises a number of steps. The first step is for the heart sound analyzer 102 to collect a fixed number (e.g., K) of incoming mixture samples in a single frame. The second step is for the heart sound analyzer 102 to calculate the updates to be made to the weights ($w_{01}$, $w_{11}$, $w_{12}$, $w_{02}$, $w_{22}$ and $w_{21}$) 416, 420, 424, 418, 422, and 426, and propagation delay differences ($b_{12}$ and $b_{21}$) 414 and 412 by iterating over the frame once. This is equivalent to averaging K gradients and updating the weights ($w_{01}$, $w_{11}$, $w_{12}$, $w_{02}$, $w_{22}$ and $w_{21}$) 416, 420, 424, 418, 422, and 426, and propagation delay differences ($b_{12}$ and $b_{21}$) 414 and 412. The third step is for the heart sound analyzer 102 to repeat the first and second steps until a predetermined number of iterations over a frame have been completed, or the updates to weights ($w_{01}$, $w_{11}$, $w_{12}$, $w_{02}$, $w_{22}$ and $w_{21}$) 416, 420, 424, 418, 422, and 426, and propagation delay differences ($b_{12}$ and $b_{21}$) 414 and 412 have become smaller than a predetermined threshold. The fourth step is for the heart sound analyzer 102 to input the next frame, which comprises new incoming data, and discard the last frame. By overlapping successive frames, convergence of the weights ($w_{01}$, $w_{11}$, $w_{12}$, $w_{02}$, $w_{22}$ and $w_{21}$) 416, 420, 424, 418, 422, and 426, and propagation delay differences ($b_{12}$ and $b_{21}$) 414 and 412 may be smoother. The fifth step is for the heart sound analyzer 102 to repeat the first, second, third, and fourth steps until the weights ($w_{01}$, $w_{11}$, $w_{12}$, $w_{02}$, $w_{22}$ and $w_{21}$) 416, 420, 424, 418, 422, and 426, and propagation delay differences ($b_{12}$ and $b_{21}$) 414 and 412 have converged to constants.

Referring to FIG. 5, the neural network 402 receives the composite heart sound signals ($x_1$ and $x_2$) 404 and 406 as inputs. A recursive parameter adjustment algorithm 502 also receives the heart sound signals ($x_1$ and $x_2$) 404 and 406 as inputs. The neural network 402 produces the estimates ($u_1$ and $u_2$) 408 and 410 and the signals ($y_1$ and $y_2$) 432 and 434. The recursive parameter adjustment algorithm 502 receives the estimates ($u_1$ and $u_2$) 408 and 410 and the signals ($y_1$ and $y_2$) 432 and 434 as inputs. The recursive parameter adjustment algorithm 502 serves to determine the parameters (e.g., the weights and delay differences) of the neural network 402.

Figure 7:
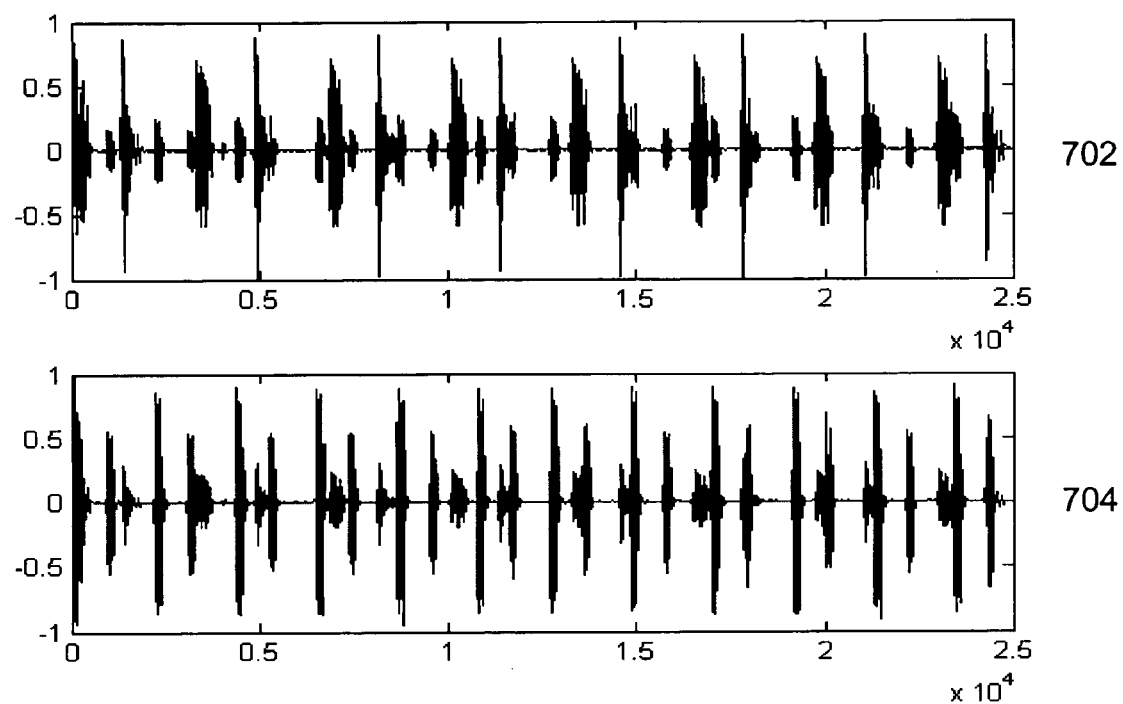
FIG. 7 is a representation of another exemplary plot of heart sound information representing the output of two sensors of the plurality of sensors of the apparatus of FIG. 1. Two fetal heart sounds are delayed by propagation delays between the fetal hearts and the plurality of sensors and then mixed by each of the plurality of sensors.
Figure 8:
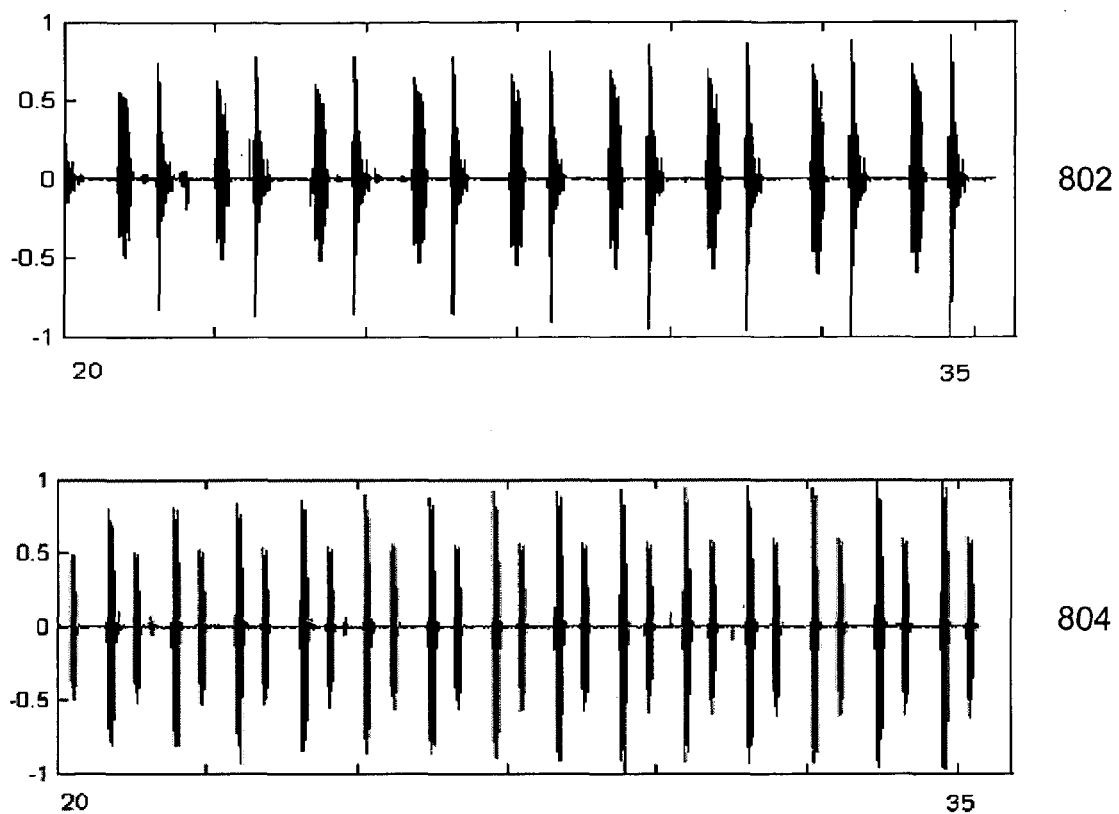
FIG. 8 is a representation of another exemplary plot of two fetal phonocardiograms extracted from heart sound information by the heart sound analyzer of the apparatus of FIG. 1.

Referring to FIGS. 1 and 6-8, fetal phonocardiograms 602 and 604 illustrate heart sounds of two fetal hearts. FIG. 7 depicts heart sound information 702 and 704 comprised of mixtures of heart sounds of the two fetal hearts delayed by propagation delays between the fetal hearts and the sensors. Fetal phonocardiograms 802 and 804 illustrate a separation of the heart sounds of the two fetal hearts from the mixed phonocardiograms 702 and 704. For example, the heart sound information 122 comprises the two phonocardiogram mixtures 702 and 704. The heart sound analyzer 102 extracts the heart sound of each of the two fetuses into statistically independent outputs.

The apparatus 100 in one example comprises a plurality of components such as one or more of electronic components, hardware components, and computer software components. A number of such components can be combined or divided in the apparatus 100. An exemplary component of the apparatus 100 employs and/or comprises a set and/or series of computer instructions written in or implemented with any of a number of programming languages, as will be appreciated by those skilled in the art.

The apparatus 100 in one example employs one or more computer-readable signal-bearing media. Examples of a computer-readable signal-bearing medium for the apparatus 100 comprise the recordable data storage medium 146 of the heart sound analyzer 102. For example, the computer-readable signal-bearing medium for the apparatus 100 comprises one or more of a magnetic, electrical, optical, biological, and atomic data storage medium. In one example, the computer-readable signal-bearing medium comprises a modulated carrier signal transmitted over a network comprising or coupled with the apparatus 100, for instance, one or more of a telephone network, a local area network ("LAN"), the internet, and a wireless network.

The steps or operations described herein are just exemplary. There may be many variations to these steps or operations without departing from the spirit of the invention. For instance, the steps may be performed in a differing order, or steps may be added, deleted, or modified.

Although exemplary implementations of the invention have been depicted and described in detail herein, it will be apparent to those skilled in the relevant art that various modifications, additions, substitutions, and the like can be made without departing from the spirit of the invention and these are therefore considered to be within the scope of the invention as defined in the following claims.

What is claimed is:

1. An apparatus, comprising:
a plurality of acoustic sensors having nonspecific locations on an abdomen of a mother; and
a processor that employs the plurality of acoustic sensors to obtain substantially simultaneously a respective plurality of mixtures of a plurality of fetal heart sounds of a respective plurality of fetuses;
wherein each of the plurality of fetal heart sound mixtures obtained by the processor from the plurality of acoustic sensors comprises a different mixture of the plurality of fetal heart sounds;
wherein the processor extracts any one or more of the plurality of fetal heart sounds that corresponds to a respective any one or more of the plurality of fetuses from the plurality of fetal heart sound mixtures.

2. The apparatus of claim 1, wherein the processor employs a blind source separation algorithm that accounts for respective propagation delays of the plurality of fetal heart sounds within the plurality of fetal heart sound mixtures to extract the any one or more of the plurality of fetal heart sounds that corresponds to the any one or more of the plurality of fetuses.

3. The apparatus of claim 1, wherein the processor employs an independent component analysis procedure to extract the any one or more of the plurality of fetal heart sounds that corresponds to the any one or more of the plurality of fetuses from the plurality of fetal heart sound mixtures.

4. The apparatus of claim 1, wherein the processor employs a neural network construct with a plurality of nodes in number at least equal to a number of the plurality of fetuses to extract the any one or more of the plurality of fetal heart sounds that corresponds to the any one or more of the plurality of fetuses from the plurality of fetal heart sound mixtures.

5. The apparatus of claim 1, wherein the plurality of fetuses comprises a first fetus and a second fetus, wherein the plurality of fetal heart sounds comprises a first fetal heart sound from the first fetus and a second fetal heart sound from the second fetus;
wherein the plurality of fetal heart sound mixtures comprises a first fetal heart sound mixture, a second fetal heart sound mixture, and a third fetal heart sound mixture;
wherein the first fetal heart sound mixture comprises a contribution from the first fetal heart sound from the first fetus, a contribution from the second fetal heart sound from the second fetus, and a contribution from background noise;
wherein the second fetal heart sound mixture comprises:
a contribution from the first fetal heart sound from the first fetus, different from the contribution to the first fetal heart sound mixture;

a contribution from the second fetal heart sound from the second fetus, different from the contribution to the first fetal heart sound mixture; and a contribution from the background noise, different from the contribution to the first fetal heart sound mixture;

wherein the third fetal heart sound mixture comprises:

a contribution from the first fetal heart sound from the first fetus, different from the contribution to the first fetal heart sound mixture and different from the contribution to the second fetal heart sound mixture;

a contribution from the second fetal heart sound from the second fetus, different from the contribution to the first fetal heart sound mixture and different from the contribution to the second fetal heart sound mixture; and a contribution from the background noise, different from the contribution to the first fetal heart sound mixture and different from the contribution to the second fetal heart sound mixture;

wherein the plurality of acoustic sensors comprises at least a first acoustic sensor having nonspecific location on the abdomen of the mother, a second acoustic sensor having nonspecific location on the abdomen of the mother, and a third acoustic sensor having nonspecific location on the abdomen of the mother;

wherein the processor employs the first acoustic sensor to obtain the first fetal heart sound mixture, wherein the processor employs the second acoustic sensor to obtain the second fetal heart sound mixture, wherein the processor employs the third acoustic sensor to obtain the third fetal heart sound mixture.

6. The apparatus of claim 5, wherein the processor separates the first fetal heart sound from the second fetal heart sound and the background noise and creates a statistically independent output of the first fetal heart sound through employment of the plurality of fetal heart sound mixtures.

7. The apparatus of claim 6, wherein the plurality of acoustic sensors comprises three or more microphones locatable over a womb of the abdomen of the mother at nonspecific locations for employment by the processor to capture the plurality of fetal heart sound mixtures of the plurality of fetal heart sounds to allow the processor to create the statistically independent output of the first fetal heart sound of the first fetus.

8. The apparatus of claim 1, wherein the plurality of acoustic sensors comprises a plurality of microphones in number at least equal to a number of the plurality of fetuses, wherein the plurality of microphones is locatable at nonspecific locations over a womb of a woman as the mother that carries the plurality of fetuses;

wherein the processor employs the plurality of microphones to obtain and pass the plurality of fetal heart sound mixtures to the processor.

9. The apparatus of claim 1, wherein the processor sets one or more propagation delay difference estimates for the plurality of fetal heart sounds;

wherein the processor iteratively processes the plurality of fetal heart sound mixtures to converge to the one or more propagation delay difference estimates closer to one or more true propagation delay differences of the plurality of fetal heart sounds to allow extraction of the any one or more of the plurality of fetal heart sounds that corresponds to the any one or more of the plurality of fetuses from the plurality of fetal heart sound mixtures.

10. The apparatus of claim 1, wherein the processor collects one or more samples of the plurality of fetal heart sound mixtures into a frame;

wherein the processor calculates one or more updates for one or more propagation delay difference and weight estimates for the frame until a predetermined number of processing iterations have occurred or the one or more updates to the one or more propagation delay difference and weight estimates drop below a predetermined threshold.

11. The apparatus of claim 10, wherein the one or more samples comprise one or more first samples, wherein the frame comprises a first frame, wherein the one or more updates comprise one or more first updates;

wherein after the predetermined number of processing iterations have occurred or the one or more first updates to the one or more propagation delay difference and weight estimates drop below the predetermined threshold, the processor collects one or more second samples of the plurality of fetal heart sound mixtures into a second frame;

wherein the processor calculates one or more second updates for the one or more propagation delay difference and weight estimates for the second frame until a predetermined number of iterations have occurred or the one or more second updates to the one or more propagation delay difference and weight estimates drop below a predetermined threshold.

12. The apparatus of claim 11, wherein the processor processes one or more additional frames until the one or more propagation delay difference and weight estimates substantially converge to constants that allow separation of the plurality of fetal heart sound mixtures into a plurality of independent components.

13. The apparatus of claim 1, wherein the plurality of fetuses comprises a first fetus and a second fetus, wherein the plurality of fetal heart sounds comprises a first fetal heart sound from the first fetus, wherein the first fetal heart sound of the first fetus comprises a mixture of a plurality of discrete heart sounds from a plurality of corresponding distinct heart sound sources within a heart of the first fetus;

wherein the processor extracts one or more of the plurality of discrete heart sounds from the first fetal heart sound of the first fetus;

wherein the plurality of discrete heart sounds comprise a first discrete heart sound of a first distinct sound source of the plurality of distinct heart sound sources;

wherein the plurality of discrete heart sounds comprise a second discrete heart sound of a second distinct sound source of the plurality of distinct heart sound sources;

wherein the first discrete heart sound and the second discrete heart sound occur contemporaneously in the first fetal heart sound;

wherein the processor creates statistically independent outputs of one or more of the first discrete heart sound and the second discrete heart sound.

14. An apparatus, comprising:

a plurality of sensor pods having nonspecific locations on an abdomen of a mother; and a processor that employs the plurality of sensor pods to capture substantially simultaneously a respective plurality of mixtures of a plurality of fetal heart sounds of a respective plurality of fetuses;

wherein each of the plurality of fetal heart sound mixtures obtained by the processor from the plurality of sensor pods comprises a different mixture of the plurality of fetal heart sounds;

wherein the processor extracts any one or more of the plurality of fetal heart sounds that corresponds to a respective any one or more of the plurality of fetuses from the plurality of fetal heart sound mixtures.

15. The apparatus of claim 14, wherein the plurality of sensor pods are locatable at nonspecific locations over a womb of a woman as the mother that carries the plurality of fetuses;

wherein the plurality of sensor pods comprise a first sensor pod and a second sensor pod, wherein the first and second sensor pods are independently movable over the womb at nonspecific locations for employment by the processor to capture substantially simultaneously the plurality of fetal heart sound mixtures of the plurality of fetal heart sounds of the plurality of fetuses.

16. The apparatus of claim 15, wherein the first sensor pod comprises a first plurality of microphones having a nonspecific location over the womb of the mother, wherein the second sensor pod comprises a second plurality of microphones having a nonspecific location over the womb of the mother;

wherein the first plurality of microphones combined with the second plurality of microphones comprise a number of microphones in number at least equal to a number of the plurality of fetuses.

17. The apparatus of claim 14, wherein the plurality of fetuses comprises a first fetus and a second fetus, wherein the plurality of fetal heart sounds comprises a first fetal heart sound from the first fetus and a second fetal heart sound from the second fetus;

wherein the processor employs the plurality of sensor pods having nonspecific locations on the abdomen of the mother to capture substantially simultaneously the first and second fetal heart sounds of the respective first and second fetuses, wherein the processor employs the plurality of sensor pods having nonspecific locations on the abdomen of the mother to capture the plurality of fetal heart sound mixtures of the plurality of fetal heart sounds as the first fetal heart sound from the first fetus, the second fetal heart sound from the second fetus, and background noise;

wherein each sensor pod of the plurality of sensor pods having nonspecific locations on the abdomen of the mother comprises at least three microphones for employment by the processor to separate the first fetal heart sound from the second fetal heart sound and the background noise and create a statistically independent output of the first fetal heart sound through employment of the plurality of fetal heart sound mixtures.

18. A method, comprising the steps of:

placing a plurality of sensor pods at nonspecific locations on an abdomen of a mother for employment by a processor to obtain substantially simultaneously a respective plurality of fetal heart sound mixtures of a plurality of fetal heart sounds of a respective plurality of fetuses, wherein each of the plurality of fetal heart sound mixtures obtained by the processor from the plurality of sensor pods comprises a different mixture of the plurality of fetal heart sounds; and extracting through employment of the processor any one or more of the plurality of fetal heart sounds that corresponds to a respective any one or more of the plurality of fetuses from the plurality of fetal heart sound mixtures.

19. The method of claim 18, wherein the step of placing the plurality of sensor pods at nonspecific locations on the abdomen of the mother for employment by the processor to obtain substantially simultaneously the respective plurality of fetal heart sound mixtures of the plurality of fetal heart sounds of the respective plurality of fetuses comprises the step of:

placing a plurality of sensor pods at nonspecific locations over a womb of a woman as the mother that carries the plurality of fetuses for employment by the processor to obtain substantially simultaneously the respective plurality of fetal heart sound mixtures of the plurality of fetal heart sounds;

wherein the plurality of sensor pods comprises a first sensor pod having a nonspecific location over the womb of the mother and a second sensor pod having a nonspecific location over the womb of the mother;

wherein the first sensor pod having a nonspecific location over the womb of the mother comprises a first plurality of microphones, wherein the second sensor pod having a nonspecific location over the womb of the mother comprises a second plurality of microphones, wherein the first plurality of microphones combined with the second plurality of microphones comprise a number of microphones in number at least equal to a number of the plurality of fetuses.

20. The method of claim 18, wherein the step of extracting through employment of the processor the any one or more of the plurality of fetal heart sounds that correspond to the any one or more of the plurality of fetuses from the plurality of fetal heart sound mixtures comprises the step of:

employing an independent component analysis procedure by the processor to extract the any one or more of the plurality of fetal heart sounds from the plurality of fetal heart sound mixtures.

* * * * *